(12) United States Patent
Dahla (10) Patent No.: US 7,632,267 B2
(45) Date of Patent: Dec. 15, 2009

(54) FUSE-ELECTRODE ELECTROSURGICAL APPARATUS

(75) Inventor: Robert H. Dahla, Sunnyvale, CA (US)

(73) Assignee: ArthroCare Corporation, Austin, TX (US)

( * ) Notice: Subject to any disclaimer, the term of this patent is extended or adjusted under 35 U.S.C. 154(b) by 451 days.

(21) Appl. No.: 11/176,803

(22) Filed: Jul. 6, 2005

(65) Prior Publication Data
US 2007/0010808 A1 Jan. 11, 2007

(51) Int. Cl.
*A61B 18/14* (2006.01)

(52) U.S. Cl. ............... 606/41; 606/45; 606/48; 606/49; 606/50

(58) Field of Classification Search ......... 606/27–34, 606/41, 42; 607/96–101
See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1936 | Wappler | 125/303 |
| 3,633,425 A | 1/1972 | Sanford | 73/356 |
| 3,707,149 A | 12/1972 | Hao et al. | 128/303.14 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |

(Continued)

FOREIGN PATENT DOCUMENTS

DE 3930451 A1 3/1991

(Continued)

OTHER PUBLICATIONS

Buchelt, et al. "Excimer Laser Ablation of Fibrocartilage: An In Vitro and In Vivo Study", Lasers in Surgery and Medicine, vol. 11, pp. 271-279, 1991.

(Continued)

*Primary Examiner*—Lee S Cohen
(74) *Attorney, Agent, or Firm*—Matthew Scheele; Brian Szymczak (57) ABSTRACT

An electrosurgical apparatus for performing a surgical procedure on a target site, comprising a shaft having a distal end portion, the distal end portion comprising an active electrode including a fuse leg, the fuse leg adapted to break and disable the instrument upon applying a voltage differential between the active electrode and a return electrode for a predetermined amount of time. In another embodiment, the present invention is a method of performing an electrosurgical procedure on a target tissue, comprising: placing an electrosurgical instrument in close proximity to the target tissue, the electrosurgical instrument comprising an active electrode having a pre-selected portion adapted to break and disable the instrument upon applying a voltage differential thereto for a working time; and applying the voltage differential.

19 Claims, 4 Drawing Sheets

U.S. PATENT DOCUMENTS

| | | | | |
|---|---|---|---|---|
| 4,228,800 A | | 10/1980 | Degler, Jr. et al. | 128/303 |
| 4,232,676 A | | 11/1980 | Herczog | 128/303 |
| 4,240,441 A | | 12/1980 | Khalil | 600/505 |
| 4,248,231 A | | 2/1981 | Herczog et al. | 128/303 |
| 4,301,801 A | * | 11/1981 | Schneiderman | 606/38 |
| 4,326,529 A | | 4/1982 | Doss et al. | 128/303 |
| 4,346,715 A | | 8/1982 | Gammell | 607/99 |
| 4,363,324 A | * | 12/1982 | Kusserow | 607/64 |
| 4,381,007 A | | 4/1983 | Doss | 128/303 |
| 4,418,692 A | | 12/1983 | Guay | 606/42 |
| 4,474,179 A | | 10/1984 | Koch | 606/40 |
| 4,476,862 A | | 10/1984 | Pao | 128/303 |
| 4,509,532 A | | 4/1985 | DeVries | 128/736 |
| 4,520,818 A | * | 6/1985 | Mickiewicz | 606/40 |
| 4,532,924 A | | 8/1985 | Auth et al. | 128/303 |
| 4,548,207 A | * | 10/1985 | Reimels | 606/50 |
| 4,567,890 A | | 2/1986 | Ohta et al. | 128/303 |
| 4,572,206 A | | 2/1986 | Geddes et al. | 600/505 |
| 4,580,557 A | | 4/1986 | Hertzmann | 606/12 |
| 4,587,975 A | | 5/1986 | Salo et al. | 600/506 |
| 4,590,934 A | | 5/1986 | Malis et al. | 128/303 |
| 4,593,691 A | | 6/1986 | Lindstrom et al. | 128/303 |
| 4,658,817 A | | 4/1987 | Hardy | 606/14 |
| 4,660,571 A | | 4/1987 | Hess et al. | 128/784 |
| 4,674,499 A | | 6/1987 | Pao | 128/303 |
| 4,682,596 A | | 7/1987 | Bales et al. | 128/303 |
| 4,706,667 A | | 11/1987 | Roos | 128/303 |
| 4,709,698 A | | 12/1987 | Johnston et al. | 606/41 |
| 4,727,874 A | | 3/1988 | Bowers et al. | 128/303 |
| 4,765,331 A | | 8/1988 | Petruzzi et al. | 128/303 |
| 4,785,823 A | | 11/1988 | Eggers et al. | 128/692 |
| 4,805,616 A | | 2/1989 | Pao | 128/303 |
| 4,823,791 A | | 4/1989 | D'Amelio et al. | 123/303 |
| 4,832,048 A | | 5/1989 | Cohen | 128/786 |
| 4,860,752 A | | 8/1989 | Turner | 607/102 |
| 4,898,169 A | * | 2/1990 | Norman et al. | 606/42 |
| 4,907,589 A | | 3/1990 | Cosman | 606/34 |
| 4,920,978 A | | 5/1990 | Colvin | 128/784 |
| 4,931,047 A | | 6/1990 | Broadwin et al. | 604/22 |
| 4,936,281 A | | 6/1990 | Stasz | 128/660 |
| 4,936,301 A | | 6/1990 | Rexroth et al. | 606/45 |
| 4,943,290 A | | 7/1990 | Rexroth et al. | 606/45 |
| 4,955,377 A | | 9/1990 | Lennox et al. | 607/105 |
| 4,966,597 A | | 10/1990 | Cosman | 606/50 |
| 4,967,765 A | | 11/1990 | Turner et al. | 128/785 |
| 4,976,711 A | | 12/1990 | Parins et al. | 606/48 |
| 4,979,948 A | | 12/1990 | Geddes et al. | 606/33 |
| 4,998,933 A | | 3/1991 | Eggers et al. | 606/41 |
| 5,007,908 A | | 4/1991 | Rydell | 606/47 |
| 5,009,656 A | | 4/1991 | Reimels | 606/48 |
| 5,035,696 A | | 7/1991 | Rydell | 606/47 |
| 5,047,026 A | | 9/1991 | Rydell | 606/48 |
| 5,047,027 A | | 9/1991 | Rydell | 606/48 |
| 5,057,105 A | | 10/1991 | Malone et al. | 606/28 |
| 5,057,106 A | | 10/1991 | Kasevich et al. | 606/33 |
| 5,057,743 A | | 10/1991 | Krasko et al. | 313/639 |
| 5,078,717 A | | 1/1992 | Parins et al. | 606/48 |
| 5,080,660 A | | 1/1992 | Buelna | 606/45 |
| 5,083,565 A | | 1/1992 | Parins et al. | 600/374 |
| 5,084,044 A | | 1/1992 | Quint | 606/27 |
| 5,085,659 A | | 2/1992 | Rydell | 606/47 |
| 5,088,997 A | | 2/1992 | Delahuerga et al. | 606/42 |
| 5,092,339 A | | 3/1992 | Geddes et al. | 606/505 |
| 5,098,431 A | | 3/1992 | Rydell | 606/48 |
| 5,099,840 A | | 3/1992 | Goble | 128/422 |
| 5,102,410 A | | 4/1992 | Dressel | 606/15 |
| 5,108,391 A | | 4/1992 | Flachenecker et al. | 606/38 |
| RE33,925 E | | 5/1992 | Bales et al. | 606/48 |
| 5,112,330 A | | 5/1992 | Nishigaki et al. | 606/46 |
| 5,122,138 A | | 6/1992 | Manwaring | 606/46 |
| 5,125,928 A | | 6/1992 | Parins et al. | 606/48 |
| 5,156,151 A | | 10/1992 | Imran | 600/375 |
| 5,167,659 A | | 12/1992 | Ohtomo et al. | 606/40 |
| 5,171,311 A | | 12/1992 | Rydell et al. | 606/48 |
| 5,174,304 A | | 12/1992 | Latina et al. | 607/141 |
| 5,178,620 A | | 1/1993 | Eggers et al. | 606/41 |
| 5,183,338 A | | 2/1993 | Wickersheim et al. | 374/131 |
| 5,190,517 A | | 3/1993 | Zieve et al. | 604/22 |
| 5,192,280 A | | 3/1993 | Parins | 606/48 |
| 5,195,959 A | | 3/1993 | Smith | 604/34 |
| 5,197,466 A | | 3/1993 | Marchosky et al. | 128/399 |
| 5,197,963 A | | 3/1993 | Parins | 606/46 |
| 5,207,675 A | | 5/1993 | Canady | 606/40 |
| 5,217,457 A | | 6/1993 | Delahuerga et al. | 606/42 |
| 5,217,459 A | | 6/1993 | Kamerling | 606/48 |
| 5,249,585 A | | 10/1993 | Turner et al. | 607/99 |
| 5,255,980 A | | 10/1993 | Thomas et al. | 374/161 |
| 5,261,410 A | | 11/1993 | Alfano et al. | 600/475 |
| 5,267,994 A | | 12/1993 | Gentelia et al. | 606/15 |
| 5,267,997 A | | 12/1993 | Farin et al. | 606/38 |
| 5,273,524 A | | 12/1993 | Fox et al. | 604/21 |
| 5,277,201 A | | 1/1994 | Stern | 607/98 |
| 5,281,216 A | | 1/1994 | Klicek | 606/42 |
| 5,281,218 A | | 1/1994 | Imran | 606/41 |
| 5,290,282 A | | 3/1994 | Casscells | 606/29 |
| 5,300,069 A | | 4/1994 | Hunsberger et al. | 606/37 |
| 5,306,238 A | | 4/1994 | Fleenor | 606/42 |
| 5,312,400 A | | 5/1994 | Bales et al. | 606/41 |
| 5,314,406 A | | 5/1994 | Arias et al. | 604/21 |
| 5,318,563 A | | 6/1994 | Malis et al. | 606/38 |
| 5,324,254 A | | 6/1994 | Phillips | 604/21 |
| 5,330,470 A | | 7/1994 | Hagen | 606/42 |
| 5,334,140 A | | 8/1994 | Philips | 604/35 |
| 5,334,183 A | | 8/1994 | Wuchinich | 606/46 |
| 5,334,193 A | | 8/1994 | Nardella | 606/41 |
| 5,336,220 A | | 8/1994 | Ryan et al. | 604/22 |
| 5,336,443 A | | 8/1994 | Eggers | 252/511 |
| 5,342,357 A | | 8/1994 | Nardella | 606/40 |
| 5,348,554 A | | 9/1994 | Imran et al. | 606/41 |
| 5,363,324 A | | 11/1994 | Hashimoto et al. | 365/156 |
| 5,366,443 A | | 11/1994 | Eggers et al. | 604/114 |
| 5,370,675 A | | 12/1994 | Edwards et al. | 607/101 |
| 5,374,261 A | | 12/1994 | Yoon | 604/385.01 |
| 5,375,588 A | | 12/1994 | Yoon | 128/4 |
| 5,380,277 A | | 1/1995 | Phillips | 604/33 |
| 5,380,316 A | | 1/1995 | Aita | 606/7 |
| 5,383,876 A | | 1/1995 | Nardella | 606/49 |
| 5,383,917 A | | 1/1995 | Desai et al. | 607/702 |
| 5,389,096 A | | 2/1995 | Aita | 606/15 |
| 5,395,312 A | | 3/1995 | Desai | 604/22 |
| 5,400,267 A | | 3/1995 | Denen et al. | 702/59 |
| 5,401,272 A | | 3/1995 | Perkins | 606/15 |
| 5,403,311 A | | 4/1995 | Abele et al. | 606/49 |
| 5,417,687 A | | 5/1995 | Nardella et al. | 606/32 |
| 5,419,767 A | | 5/1995 | Eggers et al. | 604/114 |
| 5,423,810 A | | 6/1995 | Goble et al. | 606/40 |
| 5,423,882 A | | 6/1995 | Jackman et al. | 607/122 |
| 5,436,566 A | | 7/1995 | Thompson et al. | 324/713 |
| 5,437,662 A | | 8/1995 | Nardella | 606/40 |
| 5,438,302 A | | 8/1995 | Goble | 331/167 |
| 5,441,499 A | | 8/1995 | Fritzsch | 606/45 |
| 5,451,224 A | | 9/1995 | Goble et al. | 606/48 |
| 5,454,809 A | | 10/1995 | Janssen | 606/41 |
| 5,458,596 A | | 10/1995 | Lax et al. | 606/31 |
| 5,458,597 A | | 10/1995 | Edwards et al. | 606/41 |
| 5,472,443 A | | 12/1995 | Cordis et al. | 606/48 |
| 5,486,161 A | | 1/1996 | Lax et al. | 604/22 |
| 5,496,312 A | | 3/1996 | Klicek | 606/34 |
| 5,496,314 A | | 3/1996 | Eggers | 606/41 |
| 5,496,317 A | | 3/1996 | Goble et al. | 606/48 |
| 5,505,730 A | | 4/1996 | Edwards et al. | 606/41 |
| 5,514,130 A | | 5/1996 | Baker | 606/41 |
| 5,542,915 A | | 8/1996 | Edwards et al. | 604/22 |
| 5,549,598 A | | 8/1996 | O'Donnell, Jr. | 606/6 |

| Patent | Kind | Date | Inventor | Class |
|---|---|---|---|---|
| 5,554,152 | A | 9/1996 | Aita | 606/7 |
| 5,556,397 | A | 9/1996 | Long et al. | 606/48 |
| 5,562,703 | A | 10/1996 | Desai | 606/210 |
| 5,569,242 | A | 10/1996 | Lax et al. | 606/42 |
| 5,571,100 | A | 11/1996 | Goble et al. | 606/41 |
| 5,573,533 | A * | 11/1996 | Strul | 606/34 |
| 5,584,872 | A | 12/1996 | LaFontaine et al. | 607/117 |
| 5,588,960 | A | 12/1996 | Edwards et al. | 604/20 |
| 5,599,350 | A | 2/1997 | Schulze et al. | 606/51 |
| 5,609,151 | A | 3/1997 | Mulier et al. | 128/642 |
| 5,633,578 | A | 5/1997 | Eggers et al. | 323/301 |
| 5,634,921 | A * | 6/1997 | Hood et al. | 606/5 |
| 5,643,304 | A | 7/1997 | Schechter et al. | 606/171 |
| 5,647,869 | A | 7/1997 | Goble et al. | 606/37 |
| 5,658,278 | A | 8/1997 | Imran et al. | 606/41 |
| 5,660,567 | A | 8/1997 | Nierlich et al. | 439/620.21 |
| 5,662,680 | A | 9/1997 | Desai | 606/210 |
| 5,676,693 | A | 10/1997 | LaFontaine et al. | 607/116 |
| 5,681,282 | A | 10/1997 | Eggers et al. | 604/114 |
| 5,683,366 | A | 11/1997 | Eggers et al. | 604/114 |
| 5,697,281 | A | 12/1997 | Eggers et al. | 604/114 |
| 5,697,536 | A | 12/1997 | Eggers et al. | 604/114 |
| 5,697,882 | A | 12/1997 | Eggers et al. | 606/34 |
| 5,697,909 | A | 12/1997 | Eggers et al. | 604/114 |
| 5,700,262 | A | 12/1997 | Acosta et al. | 606/48 |
| 5,715,817 | A | 2/1998 | Steven-Wright et al. | 600/373 |
| 5,722,975 | A | 3/1998 | Edwards et al. | 606/41 |
| 5,725,524 | A | 3/1998 | Mulier et al. | 606/41 |
| 5,749,869 | A | 5/1998 | Lindenmeier et al. | 606/34 |
| 5,749,871 | A * | 5/1998 | Hood et al. | 606/50 |
| 5,755,753 | A | 5/1998 | Knowlton | 607/98 |
| 5,766,153 | A | 6/1998 | Eggers et al. | 604/114 |
| 5,769,847 | A | 6/1998 | Panescu et al. | 606/42 |
| 5,785,705 | A | 7/1998 | Baker | 606/32 |
| 5,786,578 | A | 7/1998 | Christy et al. | 219/720 |
| 5,800,429 | A | 9/1998 | Edwards | 606/41 |
| 5,807,395 | A | 9/1998 | Mulier et al. | 606/41 |
| 5,810,764 | A | 9/1998 | Eggers et al. | 604/23 |
| 5,810,802 | A | 9/1998 | Panescu et al. | 606/31 |
| 5,810,809 | A | 9/1998 | Rydell | 606/49 |
| 5,836,875 | A | 11/1998 | Webster, Jr. | 600/374 |
| 5,843,019 | A | 12/1998 | Eggers et al. | 604/22 |
| 5,860,951 | A | 1/1999 | Eggers | 604/510 |
| 5,860,974 | A | 1/1999 | Abele | 606/41 |
| 5,860,975 | A | 1/1999 | Goble et al. | 606/45 |
| 5,871,469 | A | 2/1999 | Eggers et al. | 604/114 |
| 5,873,855 | A | 2/1999 | Eggers et al. | 604/114 |
| 5,873,877 | A | 2/1999 | McGaffigan | 606/41 |
| 5,885,277 | A | 3/1999 | Korth | 606/35 |
| 5,888,198 | A | 3/1999 | Eggers et al. | 604/114 |
| 5,891,095 | A | 4/1999 | Eggers et al. | 604/114 |
| 5,891,134 | A | 4/1999 | Goble et al. | 606/27 |
| 5,897,553 | A | 4/1999 | Mulier et al. | 606/41 |
| 5,902,272 | A | 5/1999 | Eggers et al. | 604/114 |
| 5,944,715 | A | 8/1999 | Goble et al. | 606/41 |
| 5,954,716 | A | 9/1999 | Sharkey et al. | 606/32 |
| 5,964,786 | A | 10/1999 | Ochs et al. | 607/5 |
| 6,004,319 | A | 12/1999 | Goble et al. | 606/48 |
| 6,013,076 | A | 1/2000 | Goble et al. | 606/41 |
| 6,015,406 | A | 1/2000 | Goble et al. | 606/41 |
| 6,024,733 | A | 2/2000 | Eggers et al. | 604/500 |
| 6,027,501 | A | 2/2000 | Goble et al. | 606/41 |
| 6,039,734 | A | 3/2000 | Goble et al. | 606/41 |
| 6,047,700 | A | 4/2000 | Eggers et al. | 128/898 |
| 6,056,746 | A | 5/2000 | Goble et al. | 606/48 |
| 6,063,079 | A | 5/2000 | Hovda et al. | 606/41 |
| 6,066,134 | A | 5/2000 | Eggers et al. | 606/32 |
| 6,068,628 | A | 5/2000 | Fanton et al. | 606/41 |
| 6,074,386 | A | 6/2000 | Goble et al. | 606/34 |
| 6,090,106 | A | 7/2000 | Goble et al. | 606/41 |
| 6,093,186 | A | 7/2000 | Goble | 606/34 |
| 6,102,046 | A | 8/2000 | Weinstein et al. | 128/898 |
| 6,105,581 | A | 8/2000 | Eggers et al. | 128/898 |
| 6,109,268 | A | 8/2000 | Thapliyal et al. | 128/898 |
| 6,117,109 | A | 9/2000 | Eggers et al. | 604/114 |
| 6,126,682 | A | 10/2000 | Sharkey et al. | 607/96 |
| 6,142,992 | A | 11/2000 | Cheng et al. | 606/34 |
| 6,149,620 | A | 11/2000 | Baker et al. | 604/22 |
| 6,159,194 | A | 12/2000 | Eggers et al. | 604/500 |
| 6,159,208 | A | 12/2000 | Hovda et al. | 606/41 |
| 6,162,217 | A | 12/2000 | Kannenberg et al. | 606/34 |
| 6,168,593 | B1 | 1/2001 | Sharkey et al. | 606/34 |
| 6,174,309 | B1 | 1/2001 | Wrublewski et al. | 606/45 |
| 6,179,824 | B1 | 1/2001 | Eggers et al. | 604/500 |
| 6,179,836 | B1 | 1/2001 | Eggers et al. | 606/45 |
| 6,183,469 | B1 | 2/2001 | Thapliyal et al. | 606/41 |
| 6,190,381 | B1 | 2/2001 | Olsen et al. | 606/32 |
| 6,197,021 | B1 | 3/2001 | Panescu et al. | 606/31 |
| 6,203,542 | B1 | 3/2001 | Ellsberry et al. | 606/41 |
| 6,210,402 | B1 | 4/2001 | Olsen et al. | 606/32 |
| 6,210,405 | B1 | 4/2001 | Goble et al. | 606/41 |
| 6,224,592 | B1 | 5/2001 | Eggers et al. | 606/32 |
| 6,228,078 | B1 | 5/2001 | Eggers | 606/32 |
| 6,228,081 | B1 | 5/2001 | Goble | 606/34 |
| 6,234,178 | B1 | 5/2001 | Eggers | 606/32 |
| 6,235,020 | B1 | 5/2001 | Cheng et al. | 606/34 |
| 6,237,604 | B1 | 5/2001 | Burnside et al. | 128/897 |
| 6,238,391 | B1 | 5/2001 | Olsen et al. | 606/41 |
| 6,254,600 | B1 | 7/2001 | Willink et al. | 606/41 |
| 6,261,286 | B1 | 7/2001 | Goble et al. | 606/34 |
| 6,261,311 | B1 | 7/2001 | Sharkey et al. | 607/96 |
| 6,264,652 | B1 | 7/2001 | Eggers et al. | 606/41 |
| 6,270,460 | B1 * | 8/2001 | McCartan et al. | 600/459 |
| 6,277,112 | B1 | 8/2001 | Underwood et al. | 606/32 |
| 6,280,441 | B1 | 8/2001 | Ryan | 606/45 |
| 6,283,961 | B1 | 9/2001 | Underwood et al. | 604/41 |
| 6,293,942 | B1 | 9/2001 | Goble et al. | 606/38 |
| 6,296,636 | B1 | 10/2001 | Cheng et al. | 606/32 |
| 6,296,638 | B1 | 10/2001 | Davison et al. | 606/41 |
| 6,306,134 | B1 | 10/2001 | Goble et al. | 606/42 |
| 6,308,089 | B1 | 10/2001 | von der Ruhr et al. | 600/338 |
| 6,309,387 | B1 | 10/2001 | Eggers et al. | 606/41 |
| 6,312,408 | B1 | 11/2001 | Eggers et al. | 604/114 |
| 6,322,549 | B1 | 11/2001 | Eggers et al. | 604/500 |
| 6,345,104 | B1 | 2/2002 | Daly et al. | 606/34 |
| 6,355,032 | B1 | 3/2002 | Hovda et al. | 606/32 |
| 6,363,937 | B1 | 4/2002 | Hovda et al. | 128/898 |
| 6,364,877 | B1 | 4/2002 | Goble et al. | 606/34 |
| 6,379,351 | B1 | 4/2002 | Thapliyal et al. | 606/41 |
| 6,391,025 | B1 | 5/2002 | Weinstein et al. | 606/41 |
| 6,409,722 | B1 | 6/2002 | Hoey et al. | 606/34 |
| 6,416,507 | B1 | 7/2002 | Eggers et al. | 606/32 |
| 6,416,508 | B1 | 7/2002 | Eggers et al. | 606/32 |
| 6,416,509 | B1 | 7/2002 | Goble et al. | 606/37 |
| 6,432,103 | B1 | 8/2002 | Ellsberry et al. | 606/41 |
| 6,440,129 | B1 | 8/2002 | Simpson | 606/42 |
| 6,468,274 | B1 | 10/2002 | Alleyne et al. | 606/32 |
| 6,468,275 | B1 | 10/2002 | Wampler et al. | 606/48 |
| 6,482,201 | B1 | 11/2002 | Olsen et al. | 606/41 |
| 6,514,250 | B1 | 2/2003 | Jahns et al. | 606/41 |
| 6,517,498 | B1 | 2/2003 | Burbank et al. | 600/564 |
| 6,530,922 | B2 | 3/2003 | Cosman | 606/34 |
| 6,558,382 | B2 | 5/2003 | Jahns et al. | 606/41 |
| 6,565,560 | B1 | 5/2003 | Goble et al. | 606/41 |
| 6,578,579 | B2 | 6/2003 | Burnside | 128/897 |
| 6,589,237 | B2 | 7/2003 | Woloszko et al. | 606/41 |
| 6,602,248 | B1 | 8/2003 | Sharps et al. | 606/32 |
| 6,620,156 | B1 | 9/2003 | Garito et al. | 606/50 |
| 6,632,193 | B1 | 10/2003 | Davison et al. | 604/22 |
| 6,632,220 | B1 | 10/2003 | Eggers et al. | 606/41 |
| 6,635,034 | B1 | 10/2003 | Cosmescu | 604/289 |
| 6,749,604 | B1 | 6/2004 | Eggers et al. | 606/41 |
| 6,749,608 | B2 | 6/2004 | Garito et al. | 606/45 |
| 6,770,071 | B2 | 8/2004 | Woloszko et al. | 606/41 |
| 6,780,178 | B2 | 8/2004 | Palanker et al. | 600/41 |
| 6,780,180 | B1 | 8/2004 | Goble et al. | 606/41 |

| Patent/Pub No. | Date | Inventor | Class |
|---|---|---|---|
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,866,671 B2 | 3/2005 | Tierney et al. | 606/130 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 * | 6/2005 | Edwards et al. | 606/40 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,700 B2 | 1/2006 | Hood | 451/6 |
| 6,991,631 B2 | 1/2006 | Woloszko et al. | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Ormsby et al. | 606/41 |
| 7,335,199 B2 | 2/2008 | Goble et al. | 606/41 |
| 7,344,532 B2 | 3/2008 | Goble et al. | 606/34 |
| 2001/0020166 A1 * | 9/2001 | Daly et al. | 606/34 |
| 2001/0025177 A1 | 9/2001 | Woloszko et al. | 606/46 |
| 2002/0029036 A1 | 3/2002 | Goble et al. | 606/38 |
| 2002/0042612 A1 * | 4/2002 | Hood et al. | 606/41 |
| 2002/0062123 A1 * | 5/2002 | McClurken et al. | 606/34 |
| 2002/0151882 A1 * | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 * | 1/2003 | Russell | 606/41 |
| 2003/0014047 A1 * | 1/2003 | Woloszko et al. | 606/41 |
| 2003/0028189 A1 | 2/2003 | Woloszko et al. | 604/45 |
| 2003/0088245 A1 | 5/2003 | Woloszko et al. | 606/41 |
| 2003/0158545 A1 | 8/2003 | Hovda et al. | 606/32 |
| 2003/0171743 A1 | 9/2003 | Tasto et al. | 606/32 |
| 2003/0181903 A1 * | 9/2003 | Hood et al. | 606/42 |
| 2003/0208194 A1 | 11/2003 | Hovda et al. | 606/41 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216732 A1 | 11/2003 | Truckai et al. | 606/49 |
| 2004/0024399 A1 | 2/2004 | Sharps et al. | 606/32 |
| 2004/0030330 A1 | 2/2004 | Brassell et al. | 606/41 |
| 2004/0049180 A1 | 3/2004 | Sharps et al. | 606/32 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/32 |
| 2005/0033278 A1 | 2/2005 | McClurken et al. | 606/34 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/32 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Sanders et al. | 606/32 |
| 2007/0282323 A1 | 12/2007 | Woloszko et al. | 606/41 |

FOREIGN PATENT DOCUMENTS

| | | |
|---|---|---|
| EP | 0703461 A2 | 3/1996 |
| EP | 0740926 A2 | 11/1996 |
| EP | 0 754 437 | 1/1997 |
| EP | 0 694 290 | 11/2000 |
| EP | 1134699 | 8/2003 |
| FR | 2313949 | 1/1977 |
| GB | 467502 | 6/1937 |
| GB | 2299216 | 9/1996 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| GB | 2333455 | 7/1999 |
| GB | 2406793 | 4/2005 |
| JP | 57-57802 | 4/1982 |
| JP | 57-117843 | 7/1982 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 95/34259 | 12/1995 |
| WO | 96/00042 | 1/1996 |
| WO | 97/00646 | 1/1997 |
| WO | 97/00647 | 1/1997 |
| WO | 97/18768 | 5/1997 |
| WO | 97/24073 | 7/1997 |
| WO | 97/24074 | 7/1997 |
| WO | 97/24993 | 7/1997 |
| WO | 97/24994 | 7/1997 |
| WO | 97/43971 | 11/1997 |
| WO | 97/48345 | 12/1997 |
| WO | 97/48346 | 12/1997 |
| WO | 98/07468 | 2/1998 |
| WO | 98/26724 | 6/1998 |
| WO | 98/27879 | 7/1998 |
| WO | 98/27880 | 7/1998 |
| WO | 99/20213 | 4/1999 |
| WO | 99/51155 | 10/1999 |
| WO | 99/51158 | 10/1999 |
| WO | 99/56648 | 11/1999 |
| WO | 00/00098 | 1/2000 |
| WO | 00/09053 | 2/2000 |
| WO | 01/24720 | 4/2001 |
| WO | 01/87154 | 5/2001 |
| WO | 02/36028 | 5/2002 |
| WO | 02/102255 | 12/2002 |
| WO | 03/024305 | 3/2003 |
| WO | 03/092477 | 11/2003 |

| WO | 2004/026150 | 4/2004 |
| WO | 2004/071278 | 8/2004 |
| WO | 2005/125287 | 12/2005 |
| WO | 2007/006000 | 1/2007 |
| WO | 2007/056729 | 5/2007 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
PCT International Search Report for PCT/US99/14685, 1 pg, Mailed Oct. 21, 1999.
PCT Notification of International Preliminary Examination Report for PCT/US99/14685, 4 pgs, Mailed Feb. 20, 2001.
PCT International Search Report for PCT/US98/22323, 1 pg, Mailed Mar. 3, 1999.
PCT Notification of International Preliminary Examination Report for PCT/US98/22323, 5 pgs, Mailed Nov. 28, 2000.
European Search Report for EP 98953859, 2 pgs, Jul. 2, 2001.
Supplementary European Search Report for EP 98953859, 3 pgs, Oct. 18, 2001.
PCT International Search Report for PCT/US99/18289, 1 pg, Dec. 7, 1999.
PCT Notification of International Preliminary Examination Report for PCT/US99/18289, 4 pgs, Jul. 7, 2000.
European Search Report for EP 99945039.8, 3 pgs, Oct. 1, 2001.
PCT International Search Report for PCT/US02/19261, 1 pg, Mailed Sep. 18, 2002.
PCT International Preliminary Examination Report for PCT/US02/19261, 3 pgs, Mar. 25, 2003.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT Written Opinion of the International Searching Authority for PCT/US04/03614, 4 pgs, Mailed Sep. 14, 2004.
EP Communication, European Examination Report for EP 98953859.0, 3 pgs, Jun. 14, 2004.
EP Communication, European Examination Report for EP 99945039.8, 5 pgs, May 10 2004.
PCT Notification of International Search Report and Written Opinion for PCT/US06/26321, 8pgs, Mailed Apr. 25, 2007.
PCT Notification of International Search Report and Written Opinion for PCT/US06/60618, 7pgs, Mailed Oct. 5, 2007.
Barry et al., "The Effect of Radiofrequency-generated Thermal Energy on the Mechanical and Histologic Characteristics of the Arterial Wall in Vivo: Implications of Radiofrequency Angioplasty" American Heart Journal vol. 117, pp. 332-341, 1982.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual", 15 pgs, Jul. 1991.
Cook et al., "Therapeutic Medical Devices: Application and Design", Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" Bio-Medical Engineering vol. 4, pp. 206-216, May 1969.
Elsasser, V.E. et al., "An Instrument for Transurethral Resection without Leakage of Current" Acta Medicotechnica vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" IEEE pp. 58-65, 1975.

Kramolowsky et al. "The Urological App of Electorsurgery" J. of Urology vol. 146, pp. 669-674, 1991.
Kramolowsky et al. "Use of 5F Bipolar Electrosurgical Probe in Endoscopic Urdogical Procedures" J. of Urology vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," Am J. Cardiol vol. 60, pp. 1117-1122, Nov. 1, 1987.
Malis, L., "Electrosurgery, Technical Note," J. Neursurg., vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" Cerebrovascular Surgery, vol. 1, pp. 245-260, 1985.
Malls, L., "New Trends in Microsurgery and Applied Technology," Advanced Technology in Neurosurgery, pp. 1-16, 1988.
Malis, L., "The Value of Irrigation During Bipolar Coagulation" See ARTC 21602, 1 pg, Apr. 9, 1993.
Nardella, P.C., SPIE 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" Gastroenterology vol. 74(3), pp. 527-534, 1978.
Protell et al., "Computer-Assisted Electrocoagulation: Bipolar v. Monopolar in the Treatment of Experimental Canine Gastric Ulcer Bleeding," Gastroenterology vol. 80, No. 3, pp. 451-455, 1981.
Ramsey et al., "A Comparison of Bipolar and Monopolar Diathermy Probes in Experimental Animals", Urological Research vol. 13, pp. 99-102, 1985.
Selikowitz et al., "Electric Current and Voltage Recordings on the Myocardium During Electrosurgical Procedures in Canines," Surgery, Gynecology & Obstetrics, vol. 164, pp. 219-224, Mar. 1987.
Shuman, "Bipolar Versus Monopolar Electrosurgery: Clinical Applications," Dentistry Today, vol. 20, No. 12, 7 pgs, Dec. 2001.
Slager et al. "Spark Erosion of Arteriosclerotic Plaques" Z. Kardiol. 76:Suppl. 6, pp. 67-71, 1987.
Slager et al. "Vaporization of Atheroscleroticc Plaques by Spark Erosion" JACC 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans* ", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for In Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al. "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop" Nov. 1989.

Valley Forge Scientific Corp., "Summary of Safety and Effective Information from 510K", 2pgs, 1991.

Valley Forge's New Products, CLINICA, 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202, 2000.

PCT Notification of the International Search Report and Written Opinion for PCT/US07/69856, 7pgs, Mailed Jun. 5, 2008.

UK Search Report for GB0805062.7, 1 pg, Jul. 16, 2008.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

BiLAP IFU 910026-001 Rev A for BiLAP Model 3525, J-Hook, 4 pgs, May 20, 1991.

BiLAP Generator Settings, Jun. 1991.

Tucker et al. "The interaction between electrosurgical generators, endoscopic electrodes, and tissue," Gastrointestinal Endoscopy, vol. 38, No. 2, pp. 118-122, 1992.

European Search Report for EP02773432, 3pgs, Dec. 19, 2008.

European Examination Report for EP 05024974, 4 pgs, Dec. 5, 2008.

UK Search Report for GB0800129.9, 2pgs, May 8, 2008.

European Search Report for EP 04708664.0, 5pgs, Apr. 6, 2009.

\* cited by examiner

FUSE-ELECTRODE ELECTROSURGICAL APPARATUS

BACKGROUND

1. Field of the Invention

This invention relates to an electrosurgical apparatus, in particular an electrosurgical apparatus comprising an electrode assembly including an electrode leg adapted to break and disable the apparatus upon expiration of a predetermined amount of use of the apparatus.

2. Description of the Prior Art

Figure 1:
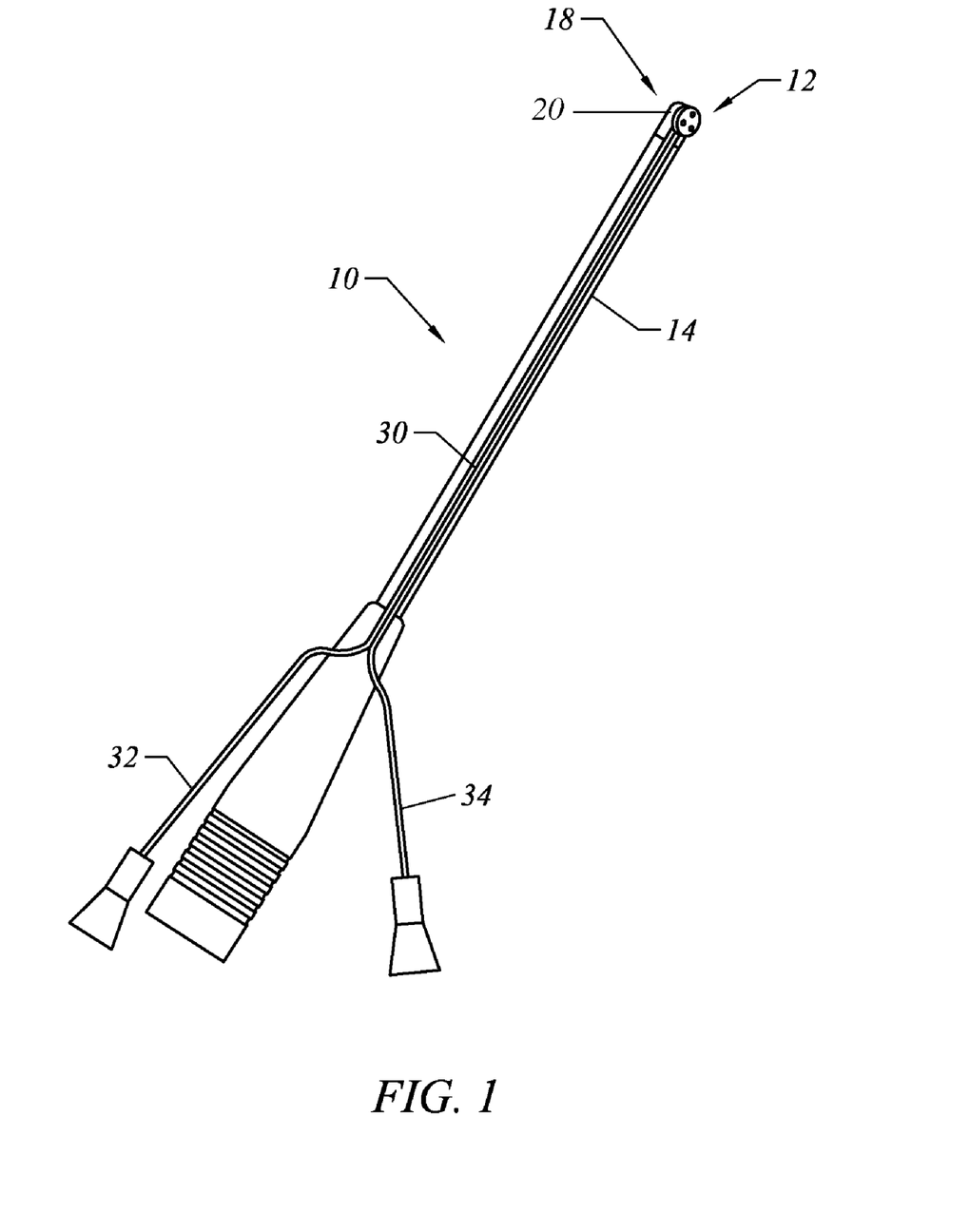
FIG. 1 is a perspective view of an electrosurgical apparatus in accordance with an embodiment of the invention.
Figure 2:
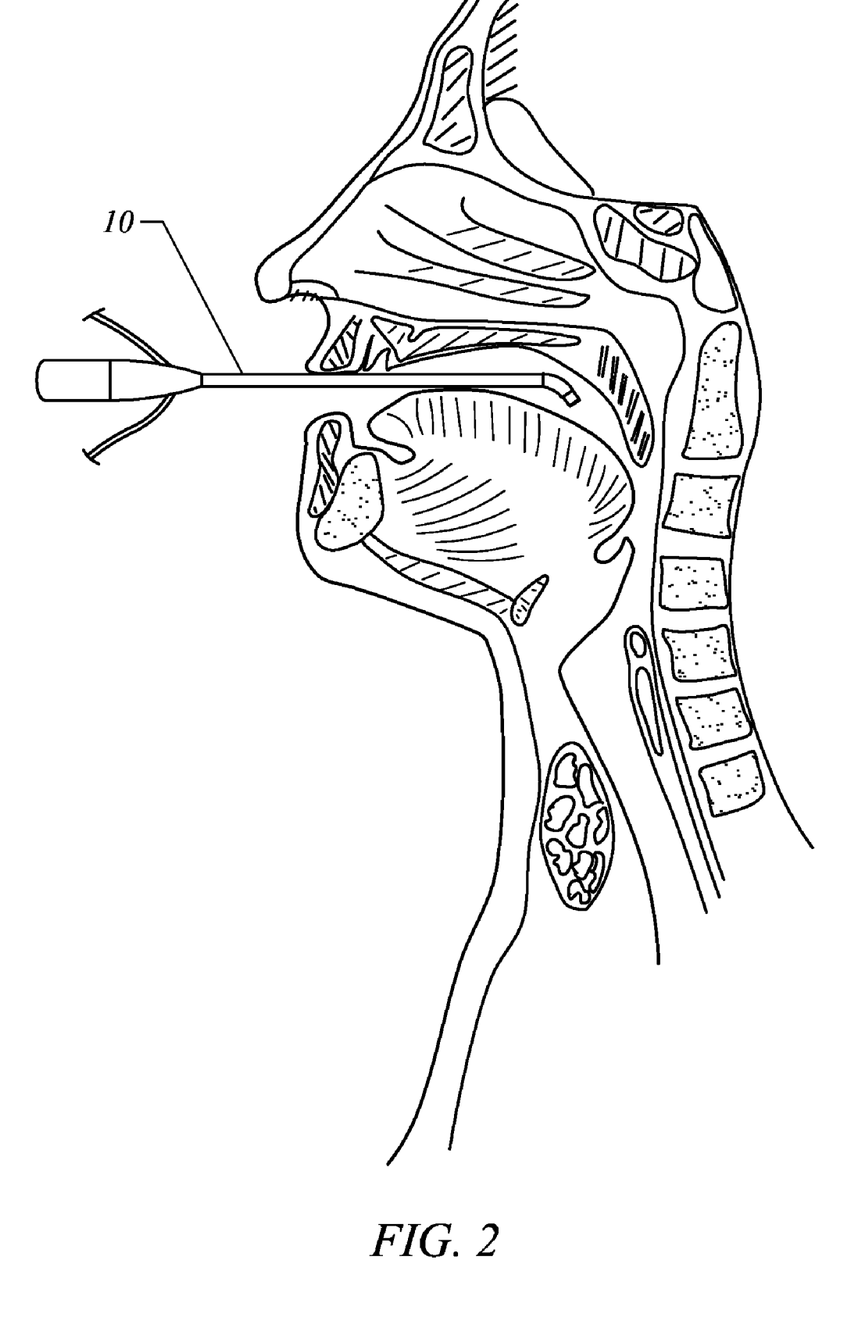
FIG. 2 is a side view of a target site in a patient being treated by an electrosurgical apparatus in accordance with an embodiment of the invention.

In electrosurgical instruments, as illustrated for example in FIG. 1, a pair of electrodes maintained at differential voltages and with dissimilar charge densities are used to conduct current to a target site to treat tissue. Treatment may include ablating, heating, cutting, removing, puncturing, probing, and otherwise stimulating tissue at the target site. The target site may include any part of a patient's body including the skin, knee, nose, spine, neck, hip, heart and the throat. See for example, U.S. Pat. No. 6,149,620 and U.S. patent application Ser. No. 09/457,201 herein fully incorporate by reference for descriptions of procedures for treating tissue at target sites using electrosurgical instruments, including procedures and instruments readily adaptable for use in accordance with the present apparatus and method.

On these instruments, the electrode with the higher charge density, referred to as the active electrode, conducts current to the target site whereas the electrode at the lower charge density, referred to as the return electrode, conducts current away from the target site. Depending on the instrument's design both electrodes may be positioned on the distal end of a shaft of the instrument in which case the instrument is referred to as a bipolar instrument. Alternatively, where only the active electrode is positioned on the shaft of the instrument and the return electrode is placed elsewhere off the instrument but in an electrical circuit with the active electrode and the target site, the instrument is referred to as monopolar instrument. In both designs, however, regardless of where the electrodes are located, for the instrument to work, it is necessary to maintain a closed electrical circuit comprising the electrodes, the target site that including a conductive media, and a high-frequency alternating voltage source.

In electrosurgical procedures, whether a monopolar or a bipolar instrument is used, treatment of the target site is effected in one of three ways: passing current through the tissue at the site; passing current through a conductive fluid on the site; or generating plasma by passing current through a conductive fluid near the target site and directing the plasma to the site. Conductive fluid includes saline and lactated ringers solution. See for example, U.S. Pat. No. 6,149,620, and U.S. patent application Ser. No. 09/457,201, supra, for description of methods of treating tissue in accordance with one or more of these procedures.

In treating a target site, an important consideration is to limit the time that the tissue is exposed to current so as to avoid unintended damage to the tissue. Another consideration is to prevent accidental reuse of disposable components of the instruments, such as the electrodes, to reduce the risk of infection. A further consideration is to avoid using an instrument having electrodes that are worn or eroded to a state such that their mechanical structures are weakened to an unacceptable level and are likely to break.

One approach to limit exposure of the tissue to excessive current, and or control wear on the electrode is to rely on the operator to monitor the time that the instrument is in use and stop treatment at an appropriate time. This may be done, for example, either manually or automatically using various timing devices on the power supply.

However, while monitoring the power supply is feasible to track the time that the tissue is exposed to current, merely monitoring the power does not indicate to the operator the extent of erosion and wear occurring on the electrodes. In this regard the applicant has discovered that as the instrument is used, the active electrode erode and wear and are likely to break. Further, depending on the material used, the dimensions of the active electrode, the type of conductive fluid used, the location of the connection to the power supply and the voltage applied to the electrodes, erosion may occur to the extent where the electrodes undesirably breaks causing bits of fragments to become lodged in the tissue. Thus, while it is possible to monitor the power to prevent over-exposure of the tissue to current, it is a problem to decide when to stop use of the instrument to avoid the undesirable consequences of erosion and wear on the electrodes and or a break on the electrodes.

One approach to monitoring the instrument for electrode erosion and wear is to visually check the physical condition of the electrodes. A problem with this approach is that because the electrodes are almost invisible to an unaided eye, it very difficult to visually determine erosion and wear. A further practical problem is that during the exigencies of a surgical procedure, a practitioner may overlook the need to periodically check the electrodes for erosion wear in time to stop using the instrument before wear becomes a problem and or the electrode breaks.

Accordingly, there is need for a more reliable way to prevent unintended and or prolonged use of the equipment, excessive exposure of the tissue to current, the consequences of a deteriorated electrode, and or the unintended reuse of disposable components of the instrument. It is thus an object of the present invention to address at least these needs.

SUMMARY OF THE INVENTION

An electrosurgical apparatus for performing a surgical procedure on a target site, comprising an active electrode assembly including a fuse leg adapted to break and disable the apparatus upon expiration of a predetermined amount of use of the apparatus. In one embodiment the electrosurgical instrument, comprises a shaft having a distal end portion, the distal end portion comprising an active electrode including a fuse leg, the fuse leg adapted to break and disable the instrument upon applying a voltage differential between the active electrode and a return electrode for a predetermined amount of time. In another embodiment, the present invention is a method of performing an electrosurgical procedure on a target tissue, comprising: placing an electrosurgical instrument in close proximity to the target tissue, the electrosurgical instrument comprising a return electrode, and an active electrode having a pre-selected portion adapted to break and disable the instrument upon applying a voltage differential between the active and return electrodes for a working time; and applying said voltage differential.

Advantageously, with the present instrument and method, a target tissue may be treated with reduced risk and consequences of a random instrument failure since the instrument is adapted to fail upon expiration of a predetermined amount of use. In various embodiments, failure is intentional due to a planned break in the electrode to incapacitate the instrument and disclosed herein.

DETAILED DESCRIPTION OF A PREFERRED EMBODIMENT

With reference to FIGS. 1-6, the present invention in one embodiment is an electrosurgical instrument (10) for performing a surgical procedure on a target site. The surgical procedure includes volumetric removal of soft tissue from the target site, for example volumetric removal of soft tissue in the throat as illustrated schematically in FIG. 2, or soft tissues at other target sites including the skin, knee, nose, spine, neck, hip, and heart.

Figure 3:
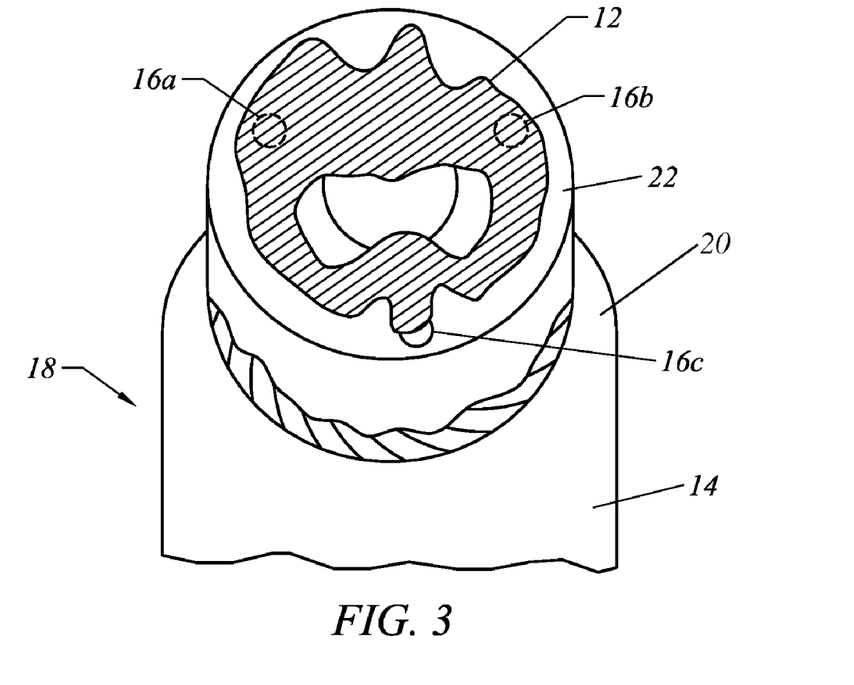
FIG. 3 is a perspective view of the distal end an electrosurgical apparatus with an intact active electrode in accordance with an embodiment of the invention.
Figure 4:
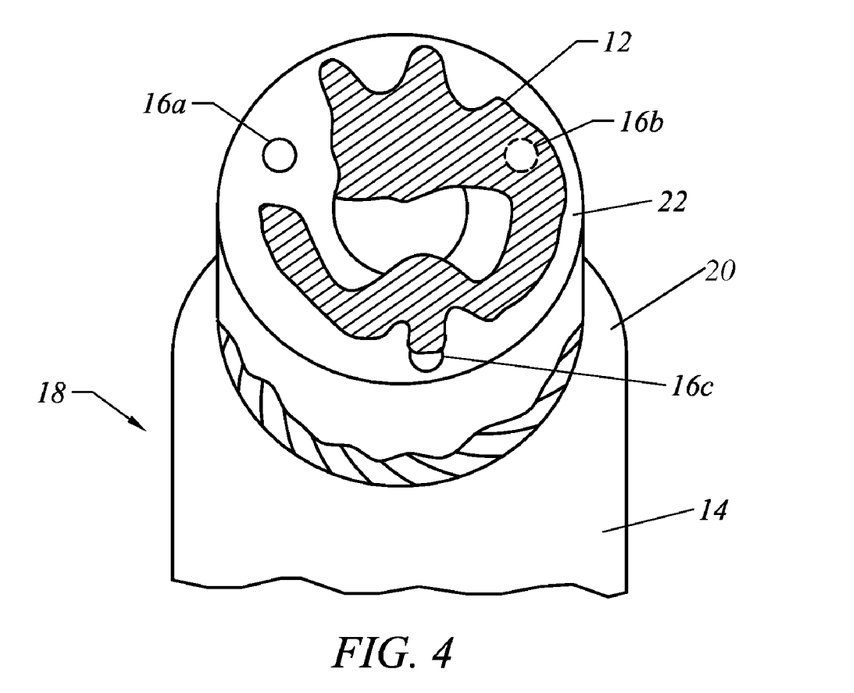
FIG. 4 is a perspective view of the distal end an electrosurgical apparatus with an eroded active electrode in accordance with an embodiment of the invention.

In one embodiment as shown schematically in FIGS. 3 and 4, the instrument comprises an active electrode assembly (12) located at the distal end (18) of a shaft (14) and includes a fuse leg (16a) sized to preferentially erode and break before a break occurs on any of the anchor legs (16b and 16c) upon expiration of a predetermined amount of use of the instrument.

In another embodiment, the invention is a method of performing an electrosurgical procedure using the instrument such that the procedure is automatically stopped after a predetermined amount of use of the instrument, due to failure on the fuse-electrode leg. In various embodiments, a predetermined amount of use includes tracking the accumulative current passing through the electrode assembly while treating a target site, as well as anticipating the erosion and wear on the fuse leg and designing the leg using appropriate materials and dimensions such that the leg will break upon a predetermined amount of use. In another embodiment, anticipation of a break on the fuse leg includes designing and adapting the leg based on the operating voltage and the conductive fluid in contact with the electrodes.

In various embodiments of the invention, the applicant is capitalizing on an observation that when the instrument is in use, erosion and wear on the active electrode occur to the extent that the erosion and wear cause a break in the electrode. Thus, the applicant is using this observation to plan for a break in an electrical circuit such that the break is used to control how much the instrument is useable, as described herein. In particular the applicant by designating a portion of the active electrode as a fuse leg, and selectively choosing the material, the operating voltage, the conductive fluid, and sizing the designated leg to conduct current through the electrode, the applicant can predetermine when to incapacitate the instrument.

While not admitting to any theory as to the cause of the erosion and or wear on the electrodes during use, it is believed that erosion and wear are attributable to an electrochemical action on the electrode due in part to the presence of a conductive fluid at the target site, and the passage of a current through the electrode in the presence of this conductive fluid. In particular, during use of the instrument, as a result of the current passing through the conductive fluid and the electrodes, plasma is formed in the vicinity of the electrodes when a voltage difference is applied between the electrodes. In one embodiment, the formation of plasma and the action of the active electrode contacting tissue at the site are correlated to the observed erosion and wear on the electrode.

Figure 6:
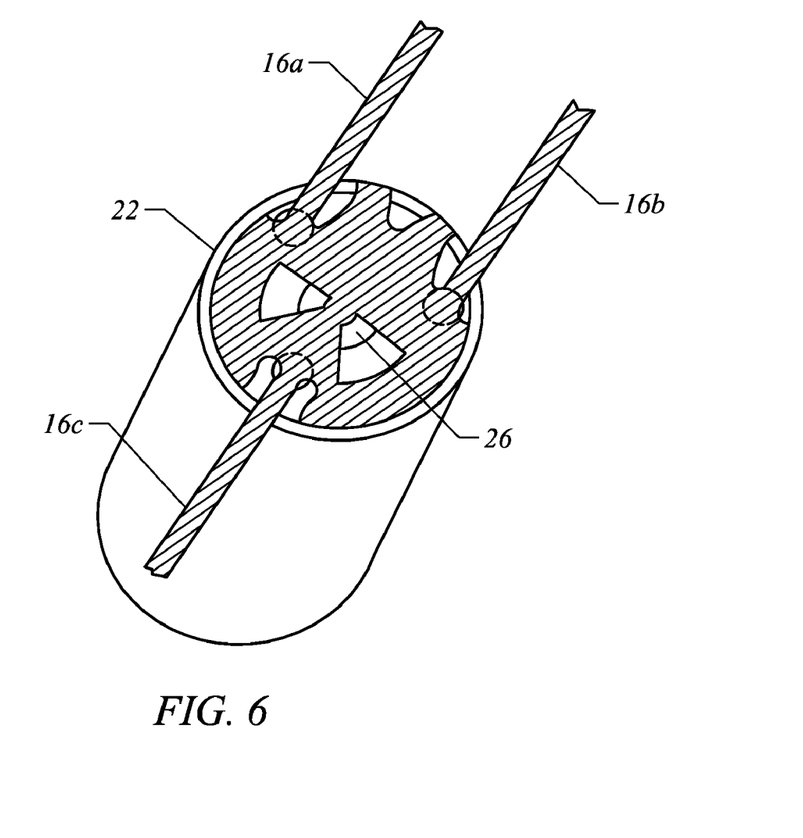
FIG. 6 is a perspective view of an active electrode being installed on an insulator in accordance with an embodiment of the invention.

In one embodiment an active electrode assembly (12) as illustrated in FIGS. 3, 4 and 6, is made of a conductive material such as platinum, tungsten, molybdenum, titanium, and corrosion resistant stainless steel. In this embodiment, the active electrode comprises a fuse leg (16a), and one or more anchor legs (16b, 16c) that together support the electrode assembly (12) on the insulator (22).

In various embodiments, the fuse electrode leg (16a) is the input path for current into the electrode assembly, and is thus electrically connected to a high frequency voltage source (not shown). To selectively promote erosion and wear on the fuse leg, several factors are controlled including: the material of the electrode, the dimensions of the electrode, the shape of the electrode, the range of voltage applied to the electrode, and the number of fuse and anchor legs. Further, it will be appreciated that the shape of the electrode assembly may vary and may take the form of a screen, a wire loop or another suitable shape; similarly, the cross-section of the electrode may vary and can be circular, cylindrical, square, oblong, disc, and or variations of these shapes.

In one embodiment the dimension of the fuse leg is selected for a width of about 0.008 inch to 0.015 inch, and a thickness of about 0.004 to about 0.007 inch. For this range of dimensions, a suitable operating voltage is about 50 volts to about 1000 volts, in particular about 200 volts to 350 volts. However it will be appreciated by one skilled in the art that in view of the description, these parameters may be varied to achieve a particular design. Similarly, the choice of material can vary; for example, a material such as platinum, tungsten, molybdenum, titanium and corrosion resistant stainless steel may be used. Similarly, the design is influenced by the desired operating time of the instrument which may vary from one hour to about 2 minutes to about 30 minutes or to about 7 minutes to about 10 minutes depending the procedure used, the amount of contact that the electrode makes with the tissue, and the flow characteristics of the conductive fluid that includes saline and lactated ringers solution.

Figure 5:
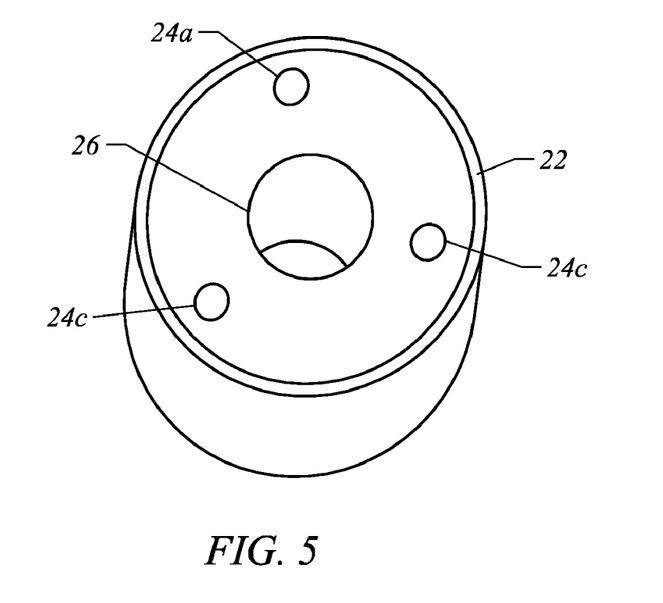
FIG. 5 is a perspective view of insulator adapted for receiving an active electrode in accordance with an embodiment of the invention.

Desirably, anchor-legs (16b, 16c) are larger than the fuse-electrode leg (16a), however as is illustrated in FIGS. 5 and 6, the actual size of each type of legs is constrained by the physical limitations of the electrode assembly (12), and the surface area (24) on the insulator to receive the electrode assembly. In designing the fuse leg to be smaller than the anchor legs it will be recognized by one skilled in the art that the fuse leg will generate a higher current density than a current density on any of the anchor legs and therefore will desirably erode at a faster rate than the anchor legs during use.

In various embodiments, the size, location, material of the fuse leg, the presence of a conductive material and the intended use of the instrument are factored together to optimize the design. Regarding size, in one embodiment a properly placed tungsten fuse of width 0.10 inches and thickness 0.007 inches will have a useful life of 7-10 minutes. Regarding location, in one embodiment the fuse leg is located in a position more likely to wear such as where power is inputted to the electrode or where the electrode is more likely to come in contact with tissue, or where the electrodes is located close to a suction lumen. On the other hand, examples of positions where the electrode is less likely to wear are those regions centrally located (most dispersed) from the return electrode, regions protected from high fluid velocity streams, and region not generally in constant contact with tissue during normal use.

As illustrated in FIGS. 3 and 4, the before-and-after effects of designing the fuse-electrode leg (16a) in accordance with the invention can be seen, for example in FIG. 3 which depicts an intact active: electrode assembly (12) anchored onto the insulator (22) prior to using the instrument, and FIG. 4 which depicts the active electrode (16a) after it has been eroded and broken, while the anchor electrodes (16b and 16c) are still intact. In the embodiment shown in FIGS. 3-6, an active electrode assembly having a fuse-electrode leg is configured to disable the instrument after a predetermined amount of use.

In one embodiment as shown in FIGS. 3-6, insulator (22) is formed of a ceramic material that defines holes (24a, 24b and 24c) in the surface for receiving fuse-electrode leg (16a) and anchor-electrode legs (16b, 16c). Additionally, insulator defines an axial aperture (26) for facilitating deployment on the distal end of shaft (14).

In one embodiment, as shown in FIG. 1, the shaft (14) includes an axial lumen (30) opened at said distal end (18) of the shaft. In this embodiment as illustrated in FIGS. 3, 4 and 6, the electrode assembly (12) comprises openings in the form of a sieve for restricting passage of materials into the lumen resulting from ablation of tissue at the distal end of the shaft (14).

In an embodiment illustrated in FIG. 1, shaft (14) further comprising an aspiration tube (32) disposed partly on the shaft for aspirating material away from the distal end. Also illustrated in FIG. 1 is a fluid supply system disposed (34) on the shaft for supplying conductive fluid to the distal end. Examples of aspiration tubes and fluid supply systems that are useable with the present apparatus are described in U.S. Pat. No. 6,149,620, and U.S. patent application Ser. No. 09/457,201, supra, and incorporated herein by reference.

As illustrated in the embodiments of FIGS. 3 and 4, return electrode (20) is provided on the shaft (14), as in a bipolar instrument, for completing the electrical connection to the voltage supply. However, return electrode may be positioned elsewhere for connection to the voltage supply as with monopolar instruments.

In another embodiment, the invention is a method of performing an electrosurgical procedure on a target location using the present apparatus. In one method the procedure involves placing the instrument proximally to a target location, and treating the target tissue with the electrode assembly until a failure at the fuse-leg incapacitates said instrument. In the method, treatment includes applying a high frequency voltage to the electrode assembly to facilitate failure at the fuse-leg during the procedure. In treating the target site, depending on whether current is passing through the target site, it may be required to direct a conductive fluid to the electrode assembly during the procedure to complete the electrical path.

As will be appreciated, the method can be used to treat target tissue includes ablating, puncturing, and cutting the target tissue. Depending on the tissue being treated, in one procedure a voltage of about 50 volts to 1000 volts can be applied; in other procedures, a voltage in the range of 200 volts to 350 volts can be applied. Also, depending on the tissue, treatment may last up to about one hour; in other procedures, treatment is about 2 minutes to about 30 minutes, more narrowly in the range of about 7 to 10 minutes. In various embodiment treatment may also include directing a conductive fluid to the target tissue so as to ablate, puncture, and cut tissue.

While the invention is described with reference to the present Figures and methods, it will be appreciated by one ordinarily skilled in the art that features of different embodiments may be combined for a particular instrument and or procedure in accordance with the present invention. Thus, alternative combination is to be considered to be within the scope of the present invention unless one feature or aspect mutually excludes the other. Accordingly, the scope of the invention should not be limited to the embodiments as described herein, but is limited only by the scope of the appended claims.

What is claimed is:

1. An electrosurgical apparatus for performing a surgical procedure on a target site, comprising an active electrode assembly electrically connected to a high frequency voltage source, the active electrode assembly including a fuse leg and one or more anchor legs, wherein said fuse leg is electrically connected to the high frequency voltage source and is smaller than the one or more anchor legs, said fuse leg configured, sized, and located such that use of the apparatus causes said fuse leg to break prior to the one or more anchor legs and upon expiration of a predetermined amount of use of said apparatus, thereby disabling said apparatus.

2. The electrosurgical apparatus of claim 1, wherein said break is controlled by optimizing a parameter selected from the group consisting of a dimension of said fuse leg, a high frequency voltage applied to said fuse leg, a material comprising said fuse leg, and a conductive fluid in contact with said fuse leg.

3. The electrosurgical apparatus of claim 2, wherein said dimension of said fuse leg is preferably a width of about 0.008 inch to 0.015 inch.

4. The electrosurgical apparatus of claim 2, wherein said high frequency voltage preferably is about 200 volts to 350 volts.

5. The electrosurgical apparatus of claim 2, wherein said material is selected from the group consisting of platinum, tungsten, molybdenum, titanium and corrosion resistant stainless steel.

6. The electrosurgical apparatus of claim 2, wherein said dimension of said fuse leg is preferably a thickness of about 0.004 to about 0.007 inch.

7. The electrosurgical apparatus of claim 1, wherein said predetermined use is about 7 minutes to about 10 minutes.

8. The electrosurgical apparatus of claim 1, wherein said fuse leg is adapted for a higher current density compared with the current density on said anchor legs.

9. The electrosurgical apparatus of claim 1, further comprising:
   a shaft having a distal end wherein said electrode assembly is disposed on said distal end;
   a return electrode disposed on said shaft proximally to said electrode assembly; and
   an insulator positioned between said return electrode and said electrode assembly for electrically insulating said return electrode from said electrode assembly.

10. The electrosurgical apparatus of claim 9, wherein said electrode assembly and said fuse leg comprise an active electrode.

11. The electrosurgical apparatus of claim 9, wherein said fuse leg is partially embedded in said insulator.

12. The electrosurgical apparatus of claim 9, wherein said shaft defines an axial lumen opened at said distal end of said shaft.

13. The electrosurgical apparatus of claim 9, further comprising an aspiration tube disposed partly on said shaft for aspirating material away from said distal end.

14. The electrosurgical apparatus of claim 13, wherein the fuse leg is located proximate to a distal opening of the aspiration tube.

15. The electrosurgical apparatus of claim 9, further including a fluid supply system disposed partly on said shaft for supplying conductive fluid to said distal end.

16. The electrosurgical apparatus of claim 15, wherein the fuse leg is located proximate to a distal opening of the fluid supply system.

17. An electrosurgical instrument, comprising: a shaft having a distal end portion, said distal end portion comprising an active electrode electrically connected to a high frequency voltage source, the active electrode including a fuse leg and one or more anchor legs, wherein said fuse leg is electrically connected to the high frequency voltage source and is smaller than the one or more anchor legs, said fuse leg configured, sized, and located to break prior to the one or more anchor legs and upon applying a voltage differential between said active electrode and a return electrode for a predetermined amount of time, thereby disabling said instrument.

18. The electrical instrument of claim 17, the one or more anchor legs for securing said active electrode on said shaft.

19. The electrical instrument of claim 17, wherein a return electrode is positioned on said shaft proximally to said active electrode; and an insulator is interposed between said return electrode and active electrode on said shaft for electrically isolating said return electrode from said active electrode.

* * * * *